(12) United States Patent
Mezzenga et al.

(10) Patent No.: US 9,012,510 B2
(45) Date of Patent: Apr. 21, 2015

(54) OLEOYLETHANOLAMIDE BASED FUNCTIONAL MESOPHASES

(75) Inventors: Rafaele Mezzenga, Zurich (CH); Sayed Mohammady, Makkah Al-Mukarrama (SA); Matthieu Pouzot, Lausanne (CH)

(73) Assignee: Nestec S.A., Vevey (CH)

( * ) Notice: Subject to any disclaimer, the term of this patent is extended or adjusted under 35 U.S.C. 154(b) by 603 days.

(21) Appl. No.: 12/935,819

(22) PCT Filed: Mar. 30, 2009

(86) PCT No.: PCT/EP2009/053729
§ 371 (c)(1),
(2), (4) Date: Apr. 26, 2011

(87) PCT Pub. No.: WO2009/121829
PCT Pub. Date: Oct. 8, 2009

(65) Prior Publication Data
US 2012/0122990 A1   May 17, 2012

(30) Foreign Application Priority Data

Apr. 2, 2008  (EP) .................................... 08153930

(51) Int. Cl.
| | | |
|---|---|---|
| *A01N 37/18* | (2006.01) | |
| *A61K 31/16* | (2006.01) | |
| *C11D 1/52* | (2006.01) | |
| *A23L 1/30* | (2006.01) | |
| *A23L 1/302* | (2006.01) | |
| *A23L 1/305* | (2006.01) | |
| *A23L 2/52* | (2006.01) | |
| *C09K 19/06* | (2006.01) | |
| *C09K 19/52* | (2006.01) | |
| *C11D 17/00* | (2006.01) | |

(52) U.S. Cl.
CPC ............... *C11D 1/523* (2013.01); *A23L 1/3008* (2013.01); *A23L 1/302* (2013.01); *A23L 1/3051* (2013.01); *A23L 2/52* (2013.01); *C09K 19/06* (2013.01); *C09K 19/52* (2013.01); *C09K 2019/528* (2013.01); *C11D 17/0026* (2013.01)

(58) Field of Classification Search
None
See application file for complete search history.

(56) References Cited

U.S. PATENT DOCUMENTS 6,066,328 A * 5/2000 Ribier et al. ................... 424/401
7,008,646 B2   3/2006 Spicer

FOREIGN PATENT DOCUMENTS

| | | |
|---|---|---|
| DE | 202004013386 | 11/2004 |
| JP | 2005525335 | 8/2005 |
| JP | 2007501115 | 1/2007 |
| JP | 2007510705 | 4/2007 |
| WO | WO2004045307 | 6/2004 |

OTHER PUBLICATIONS

Kamlekar et al., Miscibility and Phase Behavior of N-Acyltheanolamine/Diacylphosphatidylethanolamine Binary Mixtures of Matched Acyl Chainlengths (n=14, 16), Biophys. J., Jun. 1, 2007; 92(11): 3968-3977.*
Fong et al., "Diversifying the Solid State and Lyotropic Phase Behavior of Nonionic Urea-Based Surfactants," J. Phys. Chem. B 2007, 111, 10713-10722.*
Reiger et al., "Surfactants in Cosmetics 2e," Health and Fitness, 1997, p. 148.*
Patani et al., "Bioisosterism: A Rationale Approach in Drug Design," Chem. Rev. 1996, 96, 3147-3176.*
Nogrady et al., "Medicinal Chemistry: A Molecular and Biochemical Approach," p. 22 (1988, 2005) (pp. 21-22) (evidenciary reference to refute assertion of knowledge of one of ordinary skill in the art).*
Sagalowicz, et al., "Investigating reversed liquid crystalline mesopheses," Current Opinion in Colloid and Interface Science, vol. 11, No. 4, Nov. 2006, pp. 224-229, XP005765746.

* cited by examiner

*Primary Examiner* — Craig Ricci
*Assistant Examiner* — Jared D Barsky
(74) *Attorney, Agent, or Firm* — K&L Gates LLP

(57) ABSTRACT

The present invention relates to the field of liquid crystals. Embodiments of the present invention relate to liquid crystals comprising at least one molecule within N-acyl ethanolamide (NAE) family, for example oleoylethanolamide (OEA), compositions comprising them and their possible uses.

15 Claims, 5 Drawing Sheets

Arginine

Glucose

Limonene
(1-methyl-4-prop-1-en-2-yl-cyclohexene)

Oleoylethanolamide (OEA)

OLEOYLETHANOLAMIDE BASED FUNCTIONAL MESOPHASES

The present invention relates to the field of liquid crystals. Embodiments of the present invention relate to liquid crystals comprising at least one molecule of the N-acyl ethanolamide (NAE) family, for example oleoylethanolamide (OEA), compositions comprising them and their possible uses.

Recent studies in the pharmacological administration of drugs have demonstrated, that submicro-structured vehicles are far more efficient than micrometer-scaled delivery systems such as emulsion, gels, etc (A. zur Muhlen, et al., European Journal of Pharmaceutics and Biopharmaceutics, 1998, 45, 149). This has led to renewed interest for small-structured food carriers such as submicroemulsions, microemulsions and solid-lipid-submicroparticles. All of the above structures, however, have important drawbacks in their food-grade formulations. Hydrophilic compounds for example, can be delivered only by submicroemulsions and microemulsions. Submicroemulsions require extreme ultrasonification and homogenization procedures and are unstable in the long term. Microemulsions are thermodynamically stable, but strongly dependent on the surfactant used to stabilize them, which severely restricts food grade applications. Finally Solid Lipid submicroparticles are stable, but enable only the delivery of hydrophobic compounds.

In recent years, self-assembled lyotropic liquid crystalline (LC) phases of monoglycerides and water as well as their aqueous colloidal dispersions have gained increasing interest, owing to their potential in different fields of applications, such as food technology, encapsulation and crystallization of proteins, or polysaccharides, administration of drugs and for formulation of new delivery systems. The common types of liquid crystalline phases encountered in binary monoglyceride/water systems are the isotropic micellar fluid ($L_2$), the lamellar phase ($L_\alpha$), the reverse hexagonal columnar phase ($H_{II}$), and some types of reverse bicontinuous cubic structures, namely the double diamond (Pn3m), and the double gyroid (Ia3d) (Mezzenga, R.; et al., Langmuir 2005, 21, 3322). Polar guest molecules located in the aqueous domains will alter the water solution properties, and can either modify the equilibrium hydration level of the monoglyceride polar head groups, or participate directly in cooperative hydrogen bonding with the monoglyceride head groups. The research groups of Saturni and Mariani have investigated the liquid crystalline behavior of lipid-water systems in presence of large excess water, modified by trehalose saccharide as example of hydrophilic guest molecules (Saturni, L., et al., P. Phys. Rev. E 2001, 64, 040902; Mariani, et al., L. Eur. Biophys. J. Biophys. 1999, 28, 294.

Mezzenga et al. have confirmed these finding and by using dextran polysaccharide series of different molecular weights in bulk monoglyceride-water systems, have further demonstrated that the size of hydrophilic molecules plays also a role, by inducing, for example order-to-order transitions among bicontinuous cubic phases of different group spaces (Mezzenga, R, et al., Langmuir 2005, 21, 6165). On the other hand, the effect of nonpolar additives which partition preferably into the hydrophobic region of the LC systems will essentially tend to swell lipid hydrocarbon tails, release their packing frustration and increase the water/lipid curvature favouring the formation of reversed phases.

Although these liquid crystals can often be re-dispersed in water in submicrometer-sized particles, one of the major limitations in using monoglyceride-water systems as possible delivery vehicles for active ingredients is the introduction of new fat components, e.g., monoglycerides, in the resulting formulations.

For obvious nutritional considerations and current needs for obesity control, the overall amount of fatty compounds such as monoglycerides in food compositions has to be maintained low. Fat-based liquid crystals are therefore not an ideal delivery system, in particular for food applications.

Starting out from this prior art it was the object of the present invention to improve the state of the art and to provide the art with a delivery vehicle that can be used as delivery shuttle for hydrophilic and hydrophobic molecules in a polar, for example in an aqueous environment, and that at the same time will not increase the overall amount of fatty compounds and is hence also acceptable for low fat food products.

This object of the present invention could be achieved by the subject matter of the independent claims. The dependant claims further develop the present invention.

The inventors were surprised to see that a new system based on a hydrophilic solvent, e.g., water, and a special type of lipophilic bioactive, namely members of the N-acyl ethanolamide (NAE) family, for example oleoylethanolamide (OEA), allows the generation of such a delivery vehicle.

The inventors were surprised to see that lipophilic bioactive compounds such as members of the N-acyl ethanolamide (NAE) family, for example OEA, could successfully be used to prepare the liquid crystals of the present invention.

The inventors could demonstrate that (A) OEA and, e.g., water form liquid crystals re-dispersable in an aqueous phase and (B) that OEA- and, e.g., water liquid crystals can be used as delivery vehicle for hydrophilic and hydrophobic molecules in for example an aqueous environment. OEA is a natural analogue of the endogenous cannabinoid anandamide and it is naturally present for example in chocolate. Administration of OEA causes a potent and persistent decrease in food intake and gain in body mass (Thabuis, C, et al., Lipid Technology 2007, 19, 225). OEA also appears to be a lipid mediator involved in the peripheral regulation of feeding (de Fonseca, F. R., et al., Nature 2001, 414, 209).

One embodiment of the present invention relates to a novel liquid crystal comprising at least one member of the N-acyl ethanolamide (NAE) family, for example oleoylethanolamide (OEA), and a hydrophilic solvent. The hydrophilic solvent may be water, for example. The liquid crystals may be lyotropic. It was found for example that liquid crystals formed by OEA-water systems can be re-dispersed in water in the form of cubosomes.

The consumption of the novel liquid crystal will causes a potent and persistent decrease in food intake and will consequently contribute to weight management and food intake control, e.g. satiation and/or satiety.

It has consequently the exact opposite effect than fat based systems which increase the fat content of foodstuffs and are consequently increasing the energy content of foodstuffs.

The crystal may preferably be present in a typical lyotropic mesophase such as L2 phase, lamellar phase, reverse hexagonal phase, reverse Ia3d double gyroid phase, the reverse double Pn3m diamond cubic phase, reverse primitive Im3m cubic phase or in a micellar, Fd3m Cubic phase. A mixture of crystals in different phases may also be employed.

The size and crystal phase of the liquid crystal of the present invention have an impact on the stability of the liquid crystal. This nature of the crystal allows it for example to size select the crystals or to select a particular stable or less stable crystal form dependent on the intended use of the crystal.

The hydrophilic solvent and/or the liquid crystal may also contain at least one guest molecule. It may be present in the inside of the liquid crystal. This guest molecule is preferably a hydrophilic guest molecule. The nature of the preferably hydrophilic guest molecule is not critical. Any guest molecule may be selected dependant on the intended use of the final crystal. For food applications it is preferred that the at least one guest molecule is food grade. For example the inventors have demonstrated that, e.g., sugars and amino acids, for example arginine and glucose may be used as polar guest molecules.

Typical hydrophilic guest molecules that may be used in the framework of the present invention are preferably selected from the group consisting of hydrophilic amino acids, hydrophilic vitamins, sugars, hydrophilic pharmaceutically active compounds, salts, peptides and/or hydrophilic nutrients.

The preferably hydrophilic guest molecule may be present in the liquid crystal of the present invention in any amount that is technically feasible. The amounts that are typically preferred depend on the size and crystal phase of the crystal as well as on the nature of the guest molecule. It is in general, however, preferred if the guest molecule is present in the crystal in an amount up to 2.5 weight-% of the crystal, preferably 0.5-2 weight-% of the crystal, even more preferred 1-2 weight-% of the crystal.

This liquid crystal can advantageously be used, for example, as a delivery vehicle to deliver or protect guest molecules from the rather harsh environment in the mouth, stomach and/or digestive tract. The liquid crystal may consequently be used to deliver a guest molecule to a target site.

This targeted delivery may be finely tuned by the proper selection of the crystal shape and size.

The liquid crystal may also be used to mask a potential displeasing taste of a guest molecule.

A further application of the liquid crystal of the present invention is to protect valuable molecules from modification and/or degradation during long storage times.

The liquid crystal in accordance with the present invention may also comprise at least one other lipophilic compound. While these other lipophilic compounds are not particularly limited, it is preferred, that these are food grade compounds, if the liquid crystal is intended to be used in a food product. One example for such another lipophilic compound is limonene. Other suitable examples are triglycerides, unsaturated or saturated oils, essential oils, vitamins, hydrophobic aromas and flavours.

Similarly to the hydrophilic guest molecule also at least one lipophilic compound may be a guest molecule that is protected and/or delivered by the liquid crystal. Equally, for example its taste might be masked by the liquid crystal. It may also be an aroma compound by itself that imparts a certain flavour to the liquid crystal.

This other lipophilic compounds may for example also have the advantage, that they can be used to reduce the temperature that is necessary for crystal formation. This way energy can be saved in the production of the liquid crystals of the present invention.

Generally it is preferred, if the liquid crystal in accordance with the present invention comprises oleoylethanolamide (OEA) in an amount of about 0.01-99 weight-%, preferably about 1-80 weight-%, more preferably about 1-50 weight-%.

It is further preferred, if the hydrophilic solvent is present in the crystal in an amount of about 1-99.99 weight-%, preferably about 20-99.9 weight-%, more preferably about 50-99 weight-%.

It is further preferred, if the hydrophilic guest molecule is present in the crystal in an amount of about 0-30 weight-%, preferably about 0-20 weight-%, more preferably about 0-10 weight-%.

It is further preferred, if at least one other lipophilic compound is present in an amount of about 0-99 weight-%, preferably about 0-80 weight-%, more preferably about 0-10 weight-%.

The liquid crystal may be present in a solution or may equally well be prepared in a purified form. However, it is preferred if the liquid crystal in accordance with the present invention is present in dispersion or in an emulsion in a hydrophilic solvent. This contributes beneficially to the stability of the liquid crystal.

The dispersed liquid crystals particles of the present invention generally have a diameter in the range of about 1 nm to 500 μm, preferably in the range of 10 nm to 300 μm, even more preferred in the range of 50 nm to 50 μm. This small size has several advantages. It allows it for example that the relative amount of oleoylethanolamide contained in the crystal can be maximized. Further, crystals of a size of less than 100 nm are invisible even in clear solvents such as water, so that their addition for example to clear liquids can not be observed with the naked eye.

Also comprised by the present invention are compositions comprising a liquid crystal in accordance with the present invention. The nature of the composition is not particularly limited; it may be a dry or a wet composition. Preferably, however, the composition is a liquid composition.

Even more preferred, the composition comprises an emulsion, in particular a microemulsion, a submicroemulsion, a multiple emulsion, a high internal phase emulsion or mixtures thereof.

The composition may also be an emulsion, in particular a microemulsion, a submicroemulsion, a multiple emulsion, a high internal phase emulsion or a mixture thereof.

Generally an emulsion has a particle size in the range of about 100 nm to 100 μm, preferably of about 100 nm to 50 μm, even more preferred of about 1 μm to 50 μm.

A microemulsion has a particle size in the range of about 1 nm to 500 nm, preferably of about 1 nm to 200 nm, even more preferred of about 5 nm to 100 nm.

A submicroemulsion has a particle size in the range of about 10 nm to 500 nm, preferably of about 10 nm to 200 nm, even more preferred of about 10 nm to 100 nm.

Multiple emulsions are emulsions, such as water in oil emulsions, re-dispersed in a continuous phase, such as water. This leads to, for example to water-in-oil-in-water emulsions (W/O/W). These emulsions can further be redispersed in an additional phase such oil, leading to water-in-oil-in-water-in-oil emulsions (W/O/W/O). This process can be re-iterated by an arbitrary number of steps. Multiple emulsions can also be initiated by emulsifying an hydrophobic compound, such oil, in an hydrophilic medium, such as water. This leads to homologue oil-in water emulsions and multiple emulsions thereof.

High internal phase emulsions are simple emulsions in which the volume fraction of the dispersed phase exceeds 50% in volume, preferably 74%, even more preferred 80%.

For example, the composition may be a food composition, a drink, a pet food composition, a nutraceutical, a food additive, a medical composition or a cosmetical composition.

The compositions may contain other components such as, e.g., a protein source, a lipid source and/or a carbohydrate source.

The composition may also contain minerals and micronutrients such as trace elements and vitamins in accordance with the recommendations of Government bodies such as the USRDA. For example, the composition may contain per daily dose one or more of the following micronutrients in the ranges given: —300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

One or more food grade emulsifiers may be incorporated into the composition if desired; for example diacetyl tartaric acid esters of mono- and di-glycerides, lecithin The composition of the present invention may further contain hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The compositions of the present invention may be applied orally, enterally, parenterally and/or topically depending on the nature of the composition.

The small size of the crystals of the present invention even allows their parenteral administration.

The compositions and the crystals of the present invention can be used for a number of different purposes.

For example, as mentioned above, they may be used as a vehicle to deliver and/or protect compounds, such as the guest molecules mentioned above. Preferably these compounds to be delivered and/or protected are hydrophilic compounds.

They may however also additionally or alternatively be used as a vehicle to deliver and/or protect compounds, such as the at least one other lipophilic compound, for example limonene.

Due to the presence of OEA in the crystal and its properties of decreasing food intake and body mass gain, the compositions and the liquid crystals of the present invention can be used to reduce appetite and/or to induce satiety.

As a direct consequence of this, the compositions and the liquid crystals of the present invention can also be used to control weight uptake.

It is clear to those of skill in the art that they can freely combine all features listed herein without departing from the subject matter of the present invention as disclosed.

Further advantages and features of the present invention will be apparent from the following examples and figures.

Figure 4:
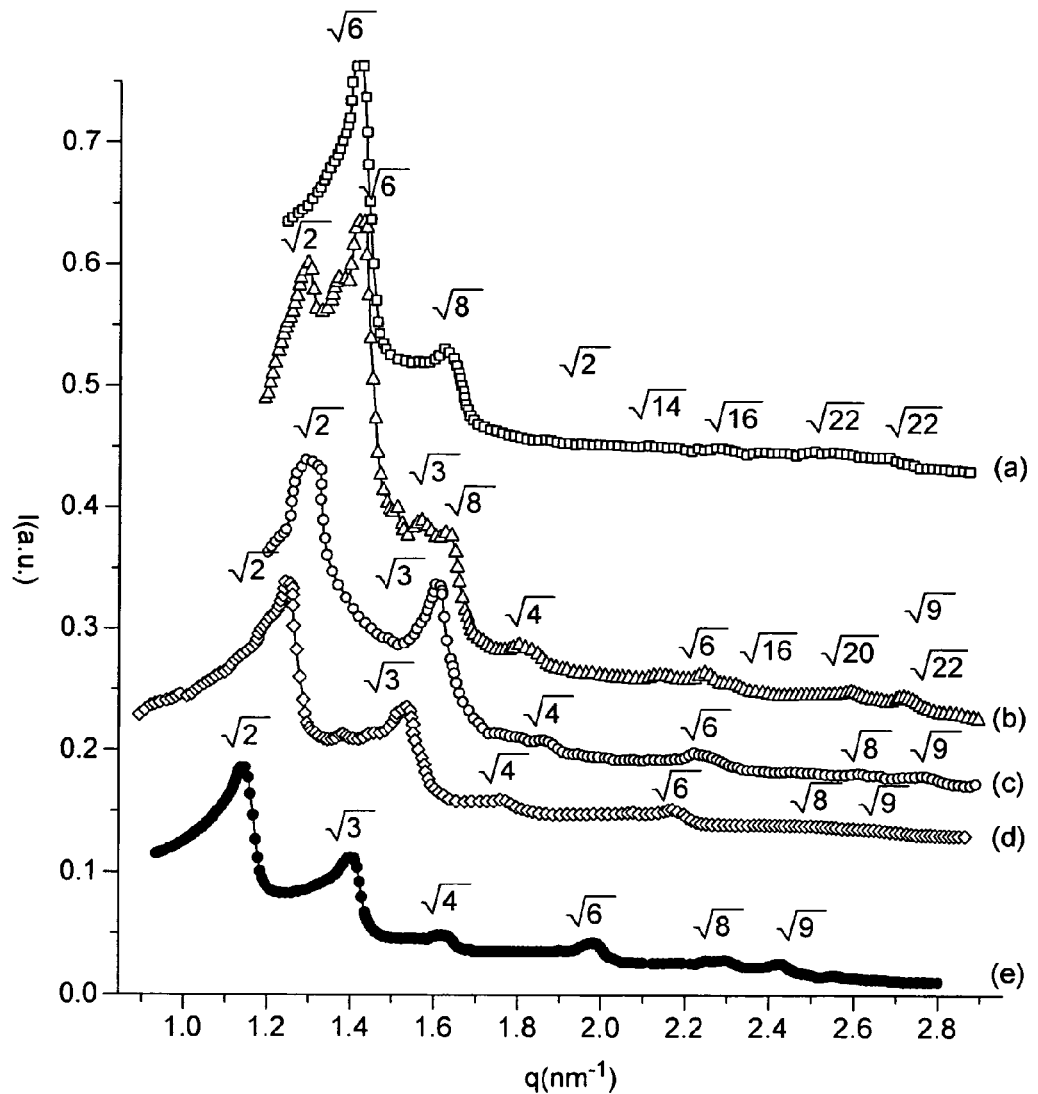

FIG. 4 shows SAXS diffractograms recorded at 42° C. for the quaternary blend OEA-limonene-water with increasing amount of arginin. The spectra (a), (b), (c), (d) correspond to a constant water to lipid ratio of 20.0% wt and arginine concentrations of 2.5, 5.0, 7.5 and 10.0 wt %, respectively. The spectrum (e) represents water to lipid ratio of 50.0% wt and arginine concentration of 5.0 wt % (dispersion of cubosomes). These diffractograms correspond to Ia3d and Pn3m cubic phases either alone or mixed in the same mesophase.

Figure 5:
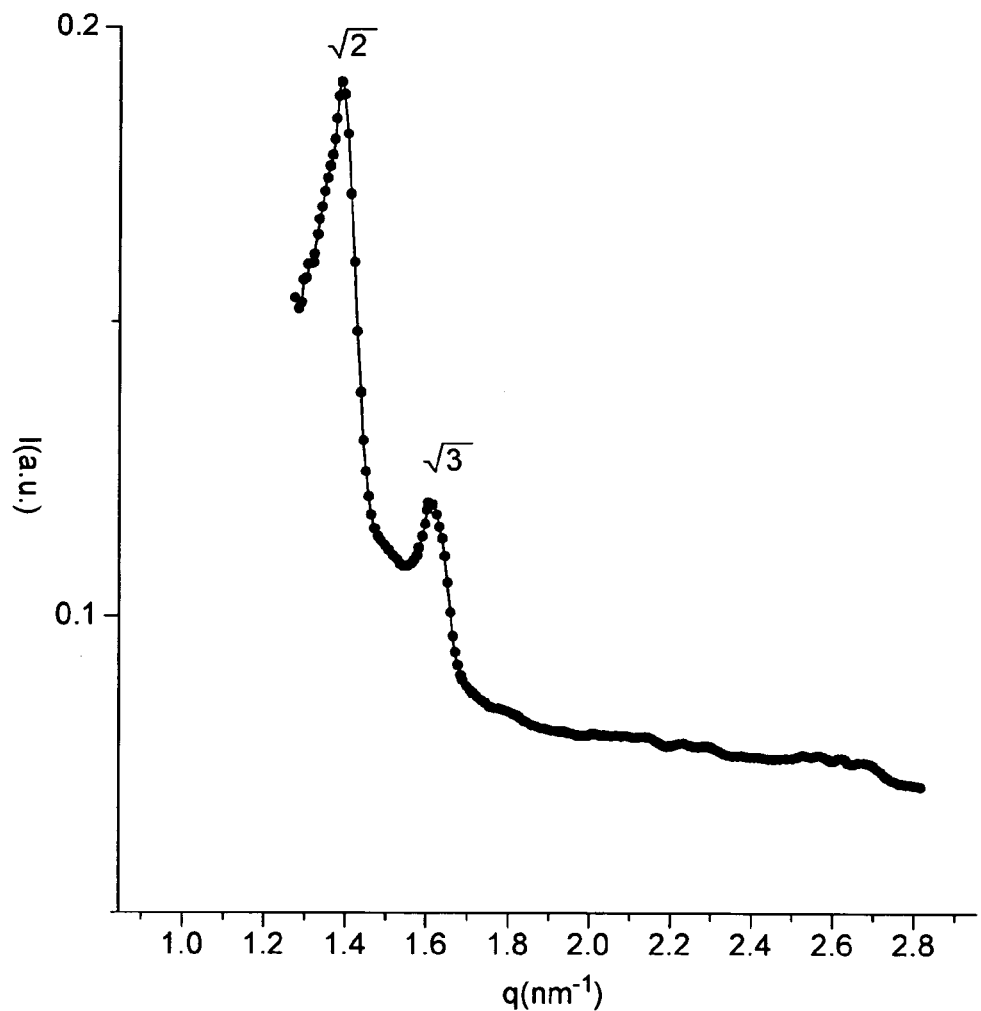

FIG. 5 shows a SAXS diffractogram at 42° C. for quaternary blend OEA-limonene-water with glucose added. The spectrum represents water to lipid ratio of 20.0% wt, and glucose concentration of 5.0% wt which corresponds to Pn3m cubic phase.

EXAMPLES

Materials Used

Figure 1:
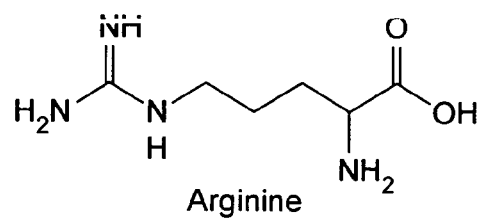
FIG. 1 shows the formulas of arginine, glucose, limonene and oleoylethanolamide (OEA)
Figure 1:
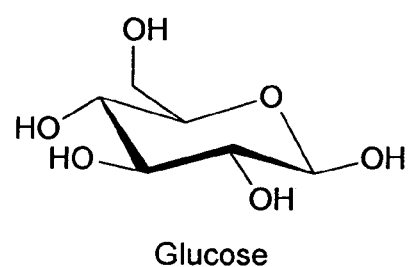
Figure 1:
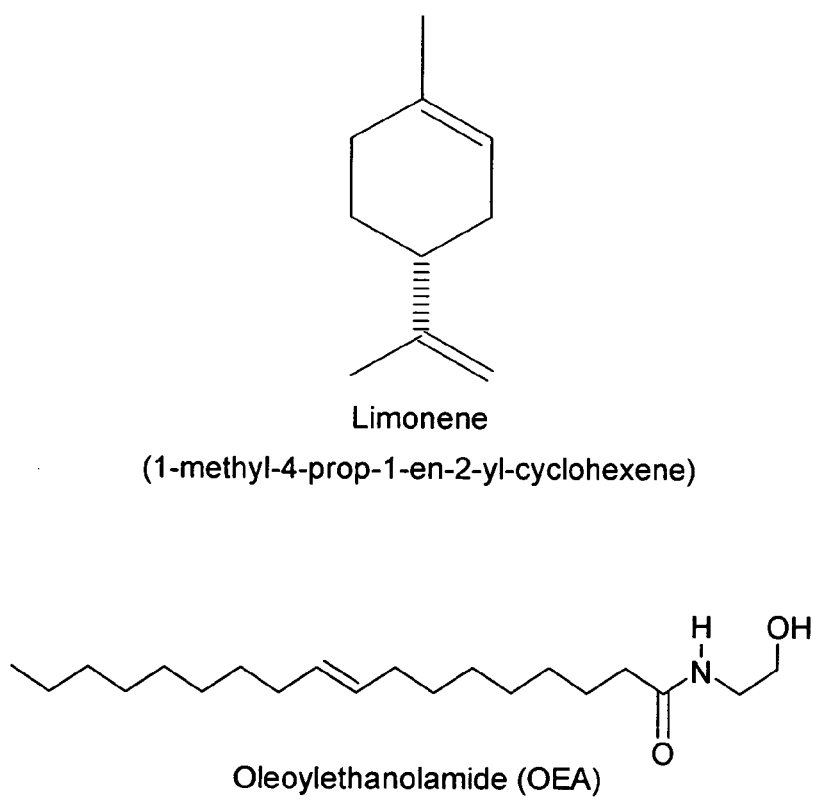

OEA was synthesized from natural raw materials and purified at Nestle Research Center. L(+)-arginine (M. wt.=174.20 g/mole), purity grade ~99%, was purchased from Aldrich, Germany. Its solubility in water was determined to be 15.91 wt % at 20° C. Limonene was used in some OEA-water formulations as an example for lipophilic guest molecule. FIG. 1 sketches the chemical structures of the various compounds used in the study.

Preparation of an OEA-Water Liquid Crystal:

In a typical OEA-water blend formulation HPLC-grade water was added to OEA at different weight ratios ranging from 10 to 50 wt %. The resulting mixtures were then placed in glass vials (15 ml volume) with sealed caps and left in water bath at 85° C. for 10 min. The vials were then subjected to vortex to shake the samples. This step was repeated twice in order to assure complete and homogeneous mixing of the components. Finally, the vials containing homogeneous samples were quenched at 4° C. to allow the study of truly equilibrium morphologies from room temperature upwards by means of small angle x-ray scattering for the identification of structures and by cross polarized optical microscopy to detect birefringence.

Figure 2:
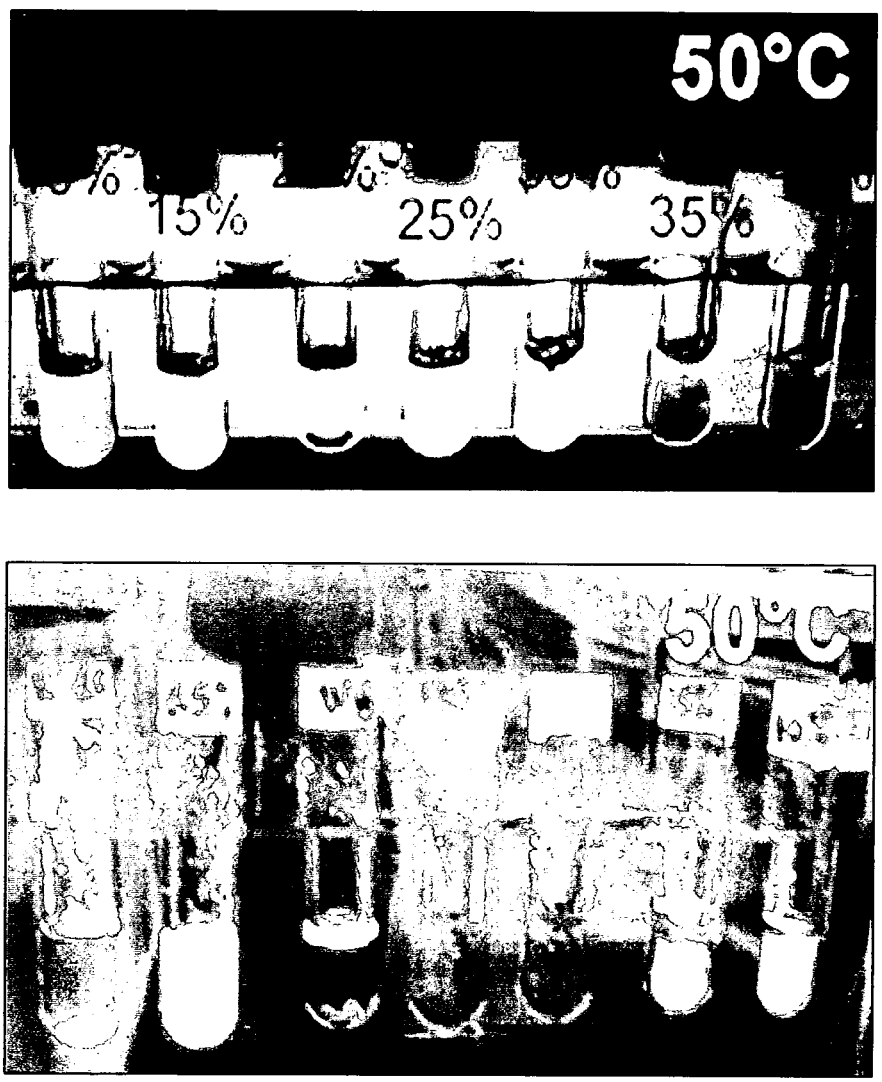
FIG. 2 shows images obtained with normal (above) and polarized microscopy (below) for binary blends OEA-water (range 10-40 wt %) at 50° C.

A phase diagram of the OEA-water blend formulations was evaluated in the range 5-50 wt % water and for temperatures between 25° C. to 85° C. SAXS measurements and cross polarized microscopy (FIG. 2) showed the presence of an inverse isotropic mesophase (L2), a viscous lamellar phase ($L_\alpha$) and rigid bicontinuous cubic phases (Pn3m and Ia3d). Cubosome dispersions of OEA could be obtained for the higher water amounts tested.

Preparation of an OEA-Water-Limonene Liquid Crystal

Figure 3:
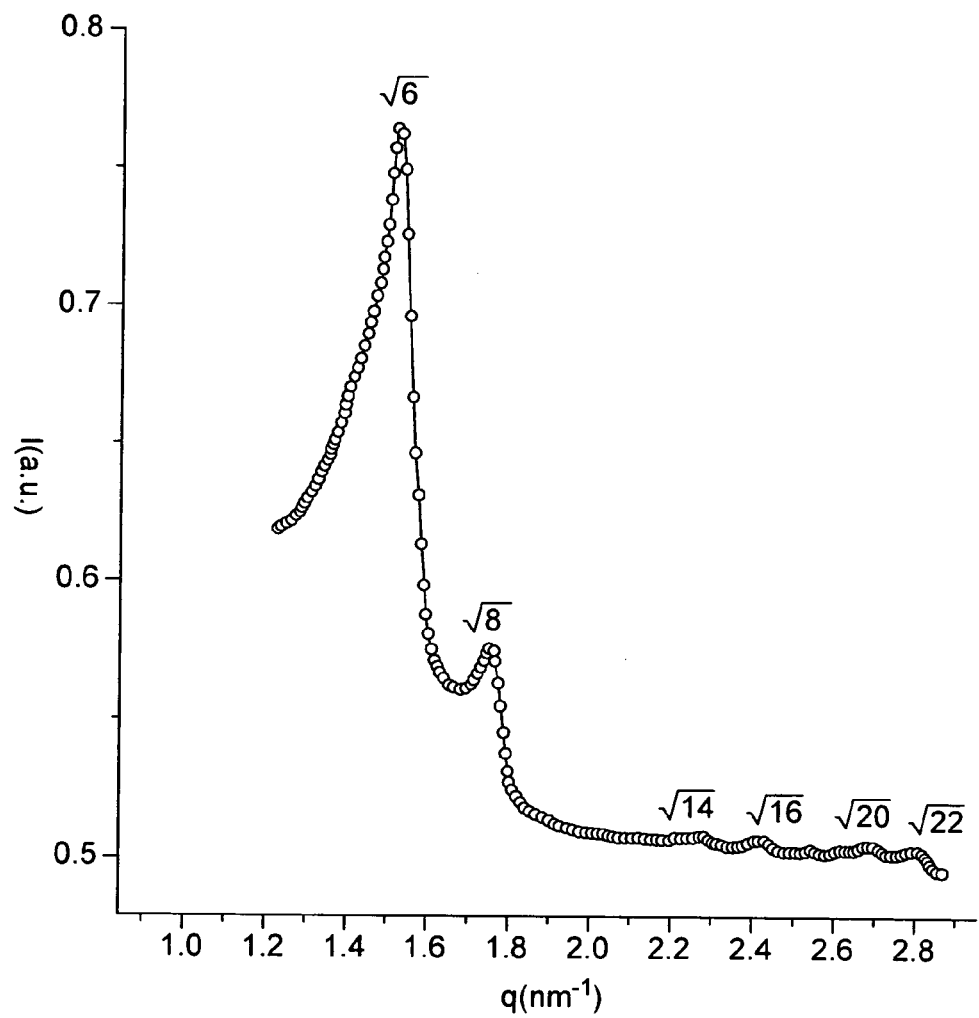
FIG. 3 shows a SAXS diffractogram for the ternary blend OEA-limonene-water for 20.0 wt.-% water at 42° C. corresponding to an Ia3d cubic phase.

In a typical limonene-OEA-water-blend formulation a small amount of limonene, i.e. 5.0 wt % with respect to OEA, was mixed with the OEA above the melting point of OEA by simple mixing. The resulting 95:5 wt % binary mixture of OEA:Limonene was then treated, for simplicity, as one single component. The formulation then was followed by addition of water, exactly as above for the OEA-water liquid crystal. Phase diagrams of the ternary mixes were obtained similarly as above for the OEA-water liquid crystal and showed the presence of inverse isotropic mesophase fluid phase (L2) and rigid bicontinuous cubic phases (Pn3m and Ia3d). Cubosomes dispersions of OEA-limonene could be obtained for the higher water amounts tested. FIG. 3 shows a SAXS diffractogram for the ternary blend OEA-limonene-water for 20.0 wt.-% water at 42° C. corresponding to an Ia3d cubic phase.

Preparation of an OEA-Water-Arginine Liquid Crystal

In a typical OEA-water-arginine formulation arginine solutions of various concentrations ranging from 0 to 10 wt % of arginine in water were prepared by dissolving arginine in HPLC-grade water at room temperature under continuous stirring. The aqueous arginine solution was then added to OEA at different weight ratios ranging from 10 to 50 wt %. The following steps of the preparations then followed the same procedure described above for the OEA-water liquid crystal. In some cases OEA contained limonene. In these cases Limonene-OEA blend preparation followed the same procedure described above for the OEA-water-limonene liquid crystal. UV absorption measurements were done to determine the concentration of released hydrophilic compounds in water. FIG. 4 shows SAXS diffractograms recorded at 42° C. for the quaternary blend OEA-limonene-water with increasing amount of arginine. The spectra (a), (b), (c), (d) correspond to a constant water to lipid ratio of 20.0% wt and arginine concentrations of 2.5, 5.0, 7.5 and 10.0 wt %, respectively. The spectrum (e) represents water to lipid ratio of 50.0% wt and arginine concentration of 5.0 wt % (dispersion of cubosomes). These diffractograms correspond to Ia3d and Pn3m cubic phases either alone or mixed in the same mesophase.

Preparation of an OEA-Water-Glucose Liquid Crystal

In a typical OEA-water-glucose formulation, glucose solutions of various concentrations ranging from 0 to 100 wt % of glucose in water were prepared by dissolving glucose in HPLC-grade water at room temperature under continuous stirring. The aqueous glucose solution was then added to OEA at different weight ratios ranging from 10 to 50 wt %. The following steps of the preparations then followed the same procedure described above for the OEA-water liquid crystal. In some cases OEA contained limonene. In these cases Limonene-OEA blend preparation followed the same procedure described above for the OEA-water-limonene liquid crystal. FIG. 5 shows a SAXS diffractogram at 42° C. for quaternary blend OEA-limonene-water with glucose added. The spectrum represents water to lipid ratio of 20.0% wt, and glucose concentration of 5.0% wt which corresponds to Pn3m cubic phase.

The invention claimed is:

1. A liquid crystal comprising oleoylethanolamide (OEA) and a hydrophilic solvent, the OEA having a particle diameter from 1 nm to 500 µm the hydrophilic solvent comprises at least one hydrophilic guest molecule that is a hydrophilic amino acid.

2. The liquid crystal in accordance with claim 1, wherein the crystal is present in a phase selected from the group consisting of typical lyotropic mesophase, lamellar phase, reverse Ia3d double gyroid phase, the reverse double Pn3m diamond cubic phase, reverse primitive Im3m cubic phase, micellar, and Fd3m Cubic phase.

3. The liquid crystal in accordance with claim 1, wherein the liquid crystal is present in a dispersion or in an emulsion in a hydrophilic solvent.

4. The liquid crystal in accordance with claim 1, wherein the hydrophilic guest molecule is present in an amount of up to 2.5 weight-% of the crystal.

5. The liquid crystal in accordance with claim 1 comprising lipophilic compounds.

6. The liquid crystal in accordance with claim 1 comprising the oleoylethanolamide (OEA) in an amount of 0.01-99 weight-%, the hydrophilic solvent in an amount of 1-99.99 weight-%, the hydrophilic guest molecule in an amount of 0-30 weight-% and a lipophilic compound in an amount of 0-50 weight-%.

7. A composition comprising a liquid crystal comprising oleoylethanolamide (OEA) and a hydrophilic solvent, the OEA having a particle diameter from 1 nm to 500 µm, the hydrophilic solvent comprises at least one hydrophilic guest molecule that is a hydrophilic amino acid.

8. The composition in accordance with claim 7, wherein the composition is in a form selected from the group consisting of a food composition, a drink, a medical composition, a cosmetical composition, a composition to be applied orally, enterally, parenterally and/or topically, an emulsion, a multiple emulsion, a high internal phase emulsion and mixtures thereof.

9. The liquid crystal in accordance with claim 1, wherein the hydrophilic guest molecule is present in an amount of 1-2 weight-% of the crystal.

10. The liquid crystal in accordance with claim 1, wherein the OEA has a particle diameter from 1 nm to 500 nm.

11. The liquid crystal in accordance with claim 1, wherein the OEA has a particle diameter from 1 nm to 200 nm.

12. The composition in accordance with claim 7, wherein the OEA has a particle diameter from 1 nm to 500 nm.

13. The composition in accordance with claim 7, wherein the OEA has a particle diameter from 1 nm to 200 nm.

14. The composition in accordance with claim 7, wherein the composition is formulated for oral administration and comprises a protein source, a lipid source and a carbohydrate source.

15. The composition in accordance with claim 14, further comprising a food grade emulsifier.

* * * * *